United States Patent [19]

Spates et al.

[11] Patent Number: 5,661,233

[45] Date of Patent: Aug. 26, 1997

[54] ACOUSTIC-WAVE SENSOR APPARATUS FOR ANALYZING A PETROLEUM-BASED COMPOSITION AND SENSING SOLIDIFICATION OF CONSTITUENTS THEREIN

[75] Inventors: James J. Spates; Stephen J. Martin; Arthur J. Mansure, all of Albuquerque, N. Mex.

[73] Assignee: Sandia Corporation, Albuquerque, N. Mex.

[21] Appl. No.: 621,929

[22] Filed: Mar. 26, 1996

[51] Int. Cl.$^6$ .......................... G01N 11/00; G01N 25/04; G01N 33/00
[52] U.S. Cl. .......................... 73/61.45; 73/54.16; 73/54.2; 374/16; 374/45; 356/70; 166/250.01
[58] Field of Search .................. 73/61.45, 54.16, 73/54.41, 54.42; 374/16, 17, 20, 45; 356/70; 166/250

[56] References Cited

U.S. PATENT DOCUMENTS

| | | | |
|---|---|---|---|
| 3,623,363 | 11/1971 | Dory | 73/194 A |
| 3,643,492 | 2/1972 | Simpson | 73/17 A |
| 3,677,064 | 7/1972 | Simpson | 73/17 R |
| 3,840,352 | 10/1974 | Scheffel | 44/62 |
| 4,115,245 | 9/1978 | Harrison et al. | 208/33 |
| 4,519,717 | 5/1985 | Jones | 374/17 |
| 4,804,274 | 2/1989 | Green | 374/17 |
| 4,925,314 | 5/1990 | Claudy | 374/16 |
| 5,007,733 | 4/1991 | Laurent | 356/70 |
| 5,088,833 | 2/1992 | Tsang | 374/17 |
| 5,201,215 | 4/1993 | Granstaff | 73/54.41 |
| 5,283,037 | 2/1994 | Baer et al. | 422/82.01 |

(List continued on next page.)

OTHER PUBLICATIONS

James N. Howell and F. W. Jessen, "Determination of the Viscosity–Temperature Relationship for Crude Oils with the Ultra–Visconson," *Journal of Petroleum Technology*, vol. 8, pp. 95–97, Sep., 1956.

V. R. Kruka, E. R. Cadena, and T. E. Long, "Cloud–Point Determination of Crude Oils," *Journal of Petroleum Technology*, vol. 47, pp. 681–687, Aug. 1995.

James J. Spates, Stephen J. Martin, Arthur J. Mansure, and Jeffrey W. Germer, "Cloud Point Determination Using a Thickness Shear Mode Resonator," presentedat the 210th Chemical Society National Meeting and Exposition, Chicago, IL, Aug. 20–24, 1995.

"ASTM Standard D 2500: Standard Test Method for Cloud Point of Petroleum Products," *Annual Book of ASTM Standards* (American Society for Testing and Materials, Philadelphia, PA), Dec. 1991.

*Primary Examiner*—Hezron E. Williams
*Assistant Examiner*—J. David Wiggins
*Attorney, Agent, or Firm*—John P. Hohimer

[57] ABSTRACT

An acoustic-wave sensor apparatus and method. The apparatus for analyzing a normally liquid petroleum-based composition includes at least one acoustic-wave device in contact with the petroleum-based composition for sensing or detecting the presence of constituents (e.g. paraffins or petroleum waxes) therein which solidify upon cooling of the petroleum-based composition below a cloud-point temperature. The acoustic-wave device can be a thickness-shear-mode device (also termed a quartz crystal mircrobalance), a surface-acoustic-wave device, an acoustic-plate-mode device or a flexural plate-wave device. Embodiments of the present invention can be used for measuring a cloud point, a pour point and/or a freeze point of the petroleum-based composition, and for determining a temperature characteristic of each point. Furthermore, measurements with the acoustic-wave sensor apparatus can be made off-line by using a sample having a particular petroleum-based composition; or in-situ with the petroleum-based composition contained within a pipeline or storage tank. The acoustic-wave sensor apparatus has uses in many different petroleum technology areas, including the recover transport, storage, refining and use of petroleum and petroleum-based products.

44 Claims, 5 Drawing Sheets

U.S. PATENT DOCUMENTS

| | | | |
|---|---|---|---|
| 5,306,644 | 4/1994 | Myerholtz et al. | 436/149 |
| 5,416,448 | 5/1995 | Wessendorf | 331/116 R |
| 5,452,232 | 9/1995 | Espinosa | 364/498 |
| 5,475,612 | 12/1995 | Espinosa | 364/500 |

ACOUSTIC-WAVE SENSOR APPARATUS FOR ANALYZING A PETROLEUM-BASED COMPOSITION AND SENSING SOLIDIFICATION OF CONSTITUENTS THEREIN

This invention was made with Government support under Contract No. DE-AC04-94AL85000 awarded by the U.S. Department of Energy. The Government has certain rights in the invention.

FIELD OF THE INVENTION

The present invention relates generally to acoustic-wave devices or sensors, and in particular to an acoustic-wave sensor apparatus and method for analyzing petroleum-based (i.e. hydrocarbon) compositions for the presence of constituents therein which solidify or crystallize below a cloud-point temperature.

BACKGROUND OF THE INVENTION

Petroleum-base compositions (e.g. crude oil and hydrocarbon compositions formed therefrom) can contain substantial amounts of petroleum waxes or paraffins. When such a normally liquid petroleum-based composition is cooled below a certain temperature referred to herein as a cloud-point temperature, the petroleum waxes or paraffins can precipitate out of the petroleum based composition forming solid particles or crystals. These solidified constituents or paraffins can then deposit on an inner surface of a pipeline resulting in a narrowing of the pipeline and restricting transport of the petroleum-based composition (e.g. crude oil during some stage of recovery, storage, transport or refining). Additionally, the paraffins can accumulate on an inner surface of a storage tank leading to a variable temperature-dependent concentration of paraffins dissolved within the petroleum-based composition. This can be disadvantageous since the accumulated paraffins can later be dissolved back into the petroleum-based composition at a high concentration when the ambient temperature exceeds the cloud-point temperature. Furthermore, the presence of dissolved paraffins can limit a temperature range for usage of petroleum-based composition (e.g. fuels such as diesel oil or gasoline, lubricants, or process feedstocks) requiring a measurement of the cloud-point temperature and some means for removing the dissolved paraffins, at least in part, to reduce the cloud-point temperature below a predetermined level.

Thus, a simple and reliable apparatus and method is needed for analyzing petroleum-based compositions and for sensing the solidification of constituents therein. Such analysis can provide information about cloud point temperature below which some of the constituents (e.g. paraffins) begin to solidify or crystallize, a pour-point temperature below which the petroleum-based composition congeals and does not readily pour or flow, and/or a freeze-point temperature at which the petroleum-based composition entirely solidifies.

Some methods for determining the cloud point for crude oils have been reviewed in an article entitled "Cloud-Point Determination for Crude Oils" by V. R. Kruka et al. (*Journal of Petroleum Technology*, vol 47, pp 618–687, August 1995) which is incorporated herein by reference. Briefly, these methods are based primary on visual observations, light transmission or scattering measurements, heat capacity and thermal conductivity measurements, density variation measurements, viscosity measurements.

An American Society for Testing and Materials (ASTM) standard test method based on visual observations is also disclosed in ASTM Standard D-2500 (Standard Test Method for Cloud Point of Petroleum Oils, pp. 199–201, ASTM, 1991). This visual observation method is limited to a relatively transparent oil sample; and it is based on an operator's subjective judgement of a temperature at which wax particles begin to appear in the oil sample, which is variable from one sample to the next and open to error. More objective cloud point measurements are possible with light-transmission or light-scattering measurements; but these measurements generally require a relatively transparent oil sample.

Viscosity cloud-point measurements have been based on measuring the energy required to produce sliding motion in a thin alloy steel blade by magnetostrictive excitation (see J. F. Nowell et al, *Journal of Petroleum Technology*, volume 8, pages 95–97, September 1956); or alternately on falling balls or rotating viscometers.

Numerous patents have also issued for determining the cloud point of oil and petroleum products, based on methods similar to those listed in the review article of Kruka et al (see U.S. Pat. Nos. 3,580,047; 3,643,492; 3,677,064; 4,519,717; 4,804,274; 4,925,314; 5,007,733; and 5,088,833).

An advantage of the apparatus and method of the present invention is that an acoustic-wave device or sensor can be used to analyze petroleum-based compositions having a wide range of viscosities and to provide information about a cloud point, a pour point, and/or a freeze point of the petroleum-based compositions.

Another advantage of the present invention is that the acoustic-wave sensor apparatus and method can be applied to analyze petroleum-based compositions in many different forms and at many different stages of oil recovery, transport, storage, processing or use; including in the form a small-volume (about 25 $cm^{-3}$) sample placed within a container; in the form of a composition flowing through a pipeline during recovery, transport, or processing; or in the form of a composition contained within a tank for storage or use.

A further advantage is that the apparatus and method of the present invention can be used to provide indications of a solidification of constituents within a pipeline or tank and of an accumulation of the solidified constituents on an inner surface of the pipeline or tank.

Still another advantage of the present, invention is that the acoustic-wave sensor apparatus can be operatively connected to means for maintaining the petroleum-based composition above a predetermined point such as a cloud point, a pour point, or a freeze point.

Yet another advantage is that the apparatus and method of the present invention provides a high measurement sensitivity, thereby allowing the determination of a plurality of cloud points within a petroleum-based composition due to different constituents which solidify at different temperature.

These and other advantages of the apparatus and method of the present invention will become evident to those skilled in the art.

SUMMARY OF THE INVENTION

An acoustic-way sensor apparatus and method are provided for analyzing a normally liquid petroleum-based composition (i.e. a hydrocarbon composition) having constituents which solidify upon being cooled below a cloud-point temperature. The apparatus comprises an acoustic-wave device or sensor having at least one surface in contact with the petroleum-based composition for detecting the presence of solidified constituents accumulated thereon and generating an output signal in response to the accumulation. The acoustic-wave sensor apparatus comprises a piezoelectric acoustic-wave device such as a thickness-shear-mode (TSM) device (also termed a quartz crystal microbalance), a surface-acoustic-wave (SAW) device, an acoustic-plate-mode (APM) device, or a flexural-plate-wave (FPW) device; and further comprises and electrical circuit for activating the acoustic-wave to generate the output signal therefrom. The acoustic-wave sensor apparatus can also include a temperature sensor in thermal contact with the petroleum-based composition for measuring the temperature thereof, and means for varying the temperature of the petroleum-based composition over a predetermined temperature range including the cloud-point temperature.

Embodiments of the present invention can be used for analyzing a sample of the petroleum-based composition placed within a container to determine information including a cloud point, a pour point, and/or a freeze point of the sample. Other embodiments of the present invention can be used for analyzing a petroleum based composition contained within a pipeline or storage tank, with the output signal from the acoustic-wave device providing information about solidification of constituents on an inner surface of the pipeline or tank; or about the attainment of a cloud point, a pour point, or a freeze point of the petroleum-based composition. Yet other embodiments of the present invention can provide an output that is operatively connected to means for maintaining the petroleum-based (i.e. hydrocarbon) composition at a predetermined point such as the cloud point, the pour point or the freeze point during recovery, transport, processing, storage or use of the petroleum-based composition.

Other objects, advantages and novel features of the invention will become apparent from the following detailed description thereof when considered in conjunction with the accompanying drawings. The objects and advantages of the invention can be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several aspects of the present invention and, together with the description, serve to explain the principles of the invention. The drawings are only for the purpose of illustrating embodiments of the invention and are not to be construed as limiting the invention. In the drawings.

DETAILED DESCRIPTION OF THE INVENTION

Figure 1:
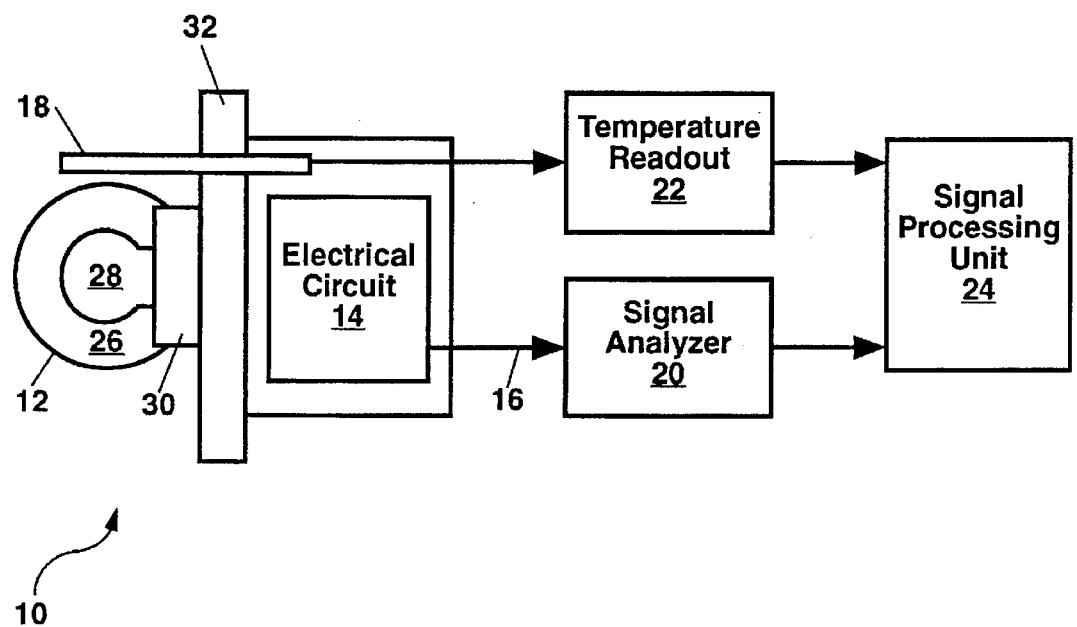
FIG. 1 shows an embodiment of an acoustic-wave sensor apparatus according to the present invention.

Referring to FIG. 1, there is shown schematically an example of an acoustic-wave sensor apparatus 10 according to the present invention. The apparatus 10 is useful for analyzing a petroleum-based composition 100 (see FIGS. 2 and 5) contacting the apparatus 10 to sense any solidification of constituents (e.g. paraffins or petroleum waxes) within the petroleum-based composition 100. The acoustic-wave sensor apparatus 10 comprises at least one acoustic-wave device 12 connected to an electrical circuit 14 for activation thereof and for generating an output signal 16 from the acoustic-wave device 12 that is responsive to an accumulation of solidified constituents on one or more surfaces of the acoustic-wave device 12 (and also to the presence of solidified constituents within the petroleum-based composition that alter a viscosity of the petroleum-based composition).

The acoustic-wave sensor apparatus 10 in some embodiments of the present invention can further include a temperature sensor 18 located proximate to the acoustic-wave device 12 as shown in FIG. 1 for sensing the temperature of the petroleum-based composition 100. The acoustic-wave sensor apparatus 10 can further include elements such as a signal analyzer 20, a temperature readout 22 and a signal processing unit 24 for display and analysis of signals from the apparatus 10. In other embodiments of the present invention, these display and analysis elements can either be provided by a user of the apparatus 10; or else they can be incorporated, at least in part, into the electrical circuit 14.

In the embodiment of the present invention depicted in FIG. 1, the acoustic-wave device 12 is shown as a thickness-shear-mode (TSM) device (also termed a quartz crystal microbalance or QCM). However, for other embodiments of the present invention the acoustic-wave device 12 can be any other type of piezoelectric acoustic-wave device as known to the art, including a surface-acoustic-wave (SAW) device, an acoustic-plate-mode (APM) device or a flexural-plate-wave (FPW) device.

In FIG. 1, the acoustic-wave device 12, in the form of a TSM device, comprises a thin wafer or plate 26 of a piezoelectric material such as an AT-cut quartz crystal with electrodes 28 formed on opposite sides of the plate 26. Because of the piezoelectric properties and crystalline orientation of the AT-cut quartz crystal plate 26, the application of a voltage between the electrodes 28 results in shear deformation of the plate 26 that excites a resonance therein when the applied voltage has in excitation frequency with an acoustic wavelength approximately equal to an odd sub-multiple of the thickness of the plate 26. At these resonant frequencies, a standing acoustic shear wave is generated across the thickness of the plate 26 for the fundamental and higher harmonic resonances. These resonant frequencies can also be altered or shifted by the presence of a material (i.e. the solidified constituents) accumulated on one or more exposed sides of e TSM acoustic-wave device 12, thereby providing a means for sensing solidified constituents within the petroleum-based composition 100.

U.S. Pat. No. 5,201,215 to Granstaff et al discloses details of a quartz crystal microbalance (QCM) or TSM device; and this patent is incorporated herein by reference. Granstaff et al consider the case of a QCM loaded from above by a surface mass layer and a contacting fluid, with the mass layer being a solid such as a metal layer rigidly attached to the QCM. Although many features of Granstaff et al are applicable to the present invention, the present invention is different from Granstaff et al in teaching operation of a TSM acoustic-wave device 12 in contact with a viscous (i.e. greater than or equal to about 10 centipoises viscosity) petroleum-based composition (i.e. a hydrocarbon composition) to measure solidified constituents accumulated on a surface of the acoustic-wave device 12 but not rigidly adhered thereto, with the solidified constituents further comprising a paraffin which is characterized by a soft or semi-rigid structure (as opposed to Granstaff et al which teaches mass layer in the form of a metal that is solid and rigidly attached to the QCM). (Paraffin is defined herein as any alkane having the generic formula $C_nH_{2n+2}$, and is used in particular to refer to higher molecular weight alkane components of petroleum-based compositions with a chain length greater than about $C_{20}$, and typically in the range of about $C_{20}$ to $C_{50}$.)

U.S. patent application Ser. No. 08/108,397 to Martin et al (Aug. 18, 1993 filing date) discloses usage of an acoustic-wave device for an in-situ measurement of the density and viscosity of working fluids such as oil in an operating engine, and is also incorporated herein by reference. The Martin et al patent application generally teaches that oscillation of an acoustic-wave device ceases for use with a fluid having a viscosity of more than about 10 centipoises (see FIG. 11 of the Martin et al patent application). However, the teaching of the present invention is that an acoustic-wave device 12 can be used for measurements within a fluid (e.g. a hydrocarbon composition) having a viscosity greater than about 10 centipoises (cP) if an improved electrical circuit 14 is used for activating the acoustic-wave device 12.

In the example of FIG. 1, the TSM acoustic-wave device 12 can be, for example, a 2.54 cm diameter, synthetic AT-cut quartz crystal plate 26. Those skilled in the art will know that other sizes, shapes, and crystalline cuts of quartz, as well as lithium niobate, and certain cuts of lithium tantalate, or any piezoelectric material that allows shear deformations to be electrically excited can be used for forming the acoustic-wave device 12.

The quartz crystal plate 26 in the example of FIG. 1 can be about 0.33 millimeters thick, with smooth side surfaces that have been lapped and polished. The electrodes 28 can be deposited and patterned on an upper and a lower side of the plate 26 by means known to the art including vacuum-deposition of an adhesion layer (e.g. about 1 to 20 nanometers or more of chromium or titanium), followed by deposition of a thin layer (e.g. about 100 to 200 nanometers) of gold or any other conductive metal.

In the example FIG. 1, each electrode 28 can have a generally circular shape (e.g. about 0.5–1.5 cm in diameter) centered on a surface of the plate 26, with a contact pad portion extending outward along the surface of the plate for providing an electrical connection to each electrode 28 for activating the TSM device 12. The electrodes 28 can have different diameters, with one of the electrodes 28 generally serving as a ground electrode; and the other electrode 28 generally serving as a radio-frequency (rf) electrode for applying an rf voltage (i.e. an rf electrical signal) and generating an oscillating electric field across the thickness of the plate 26 to excite an acoustic vibration mode therein. A coaxial cable or stripline can be used to provide an electrical connection between the TSM acoustic-wave device 12 and the electrical circuit 14 for activating the acoustic-wave device 12, with a support 30 for holding the TSM device 12 at a predetermined angle, and some cases forming at least a part of the electrical connection thereto. The support 30 can include, for example, a pair of spring-loaded contacts for contacting the contact ad portion of each electrode 28; or alternately, the support can include one or more insulated feedthroughs or the like to provide wire connections to the TSM device 12. An attachment 32 can also be provided for attaching a sensor portion of the apparatus 10 to a pipeline, tank, sample container, or the like that contains the petroleum-based composition to be analyzed.

In FIG. 1, an electrical circuit 14 can be provided proximate to the TSM acoustic-wave device 12 within a housing and electrically connected thereto for providing the rf voltage across the electrodes 28 to activate the acoustic-wave device 12. The electrical circuit 14 can be any type of oscillate circuit as known to the art for activating acoustic-wave devices. In some preferred embodiments of the present invention, the electrical circuit is a lever oscillator circuit similar in design and function to one of the circuits disclosed in U.S. Pat. No. 5,416,448 to Wessendorf, which is incorporated herein by reference. The use of a lever oscillator circuit is particularly advantageous for allowing operation of the acoustic-wave device 12 over a wide range of resonator resistance due to damping which occurs when one or more surfaces of the acoustic-wave device 12 are in contact with a liquid. Although the patent of Wessendorf discloses use of lever oscillator circuit with liquids having viscosities up to about 10 cP as is characteristic of many different petroleum-based hydrocarbon greater than 10 cP as is characteristic of many different petroleum-based hydrocarbon compositions 100, including crude oil and products refined therefrom (e.g. fuel oils, lubricants, gasoline, solvents etc.). (It should be noted that cooling of the petroleum-based composition produces solidified constituents therein that produce a slurry which further increases the viscosity of the petroleum-based composition beyond 10 centipoise.)

In the example of FIG. 1, the TSM acoustic-wave device 12 can be used as a frequency-control lever element of the oscillator circuit (i.e. the electrical circuit 14), with the lever oscillator circuit both tracking a frequency of oscillation (i.e. a resonant frequency) of the TMS acoustic-wave device 12 and providing a feedback or damping voltage to maintain an amplitude of oscillation of the TSM device 12 at a substantially constant level. In this way, the lever oscillator circuit can compensate for changes in damping of the TSM device 12 due both to changes in the viscosity of the petroleum-based composition 100 (e.g. due to solidified constituents forming therein at a temperature at or below a cloud-point temperature characteristic of a particular petroleum-based composition 100) and also to an accumulation of solidified constituents from the petroleum-based composition 100 on one or more surfaces of the TSM acoustic-wave device 12. Since both of these factors that change the viscosity of the petroleum-based composition 100 can occur at or below a cloud point thereof, one or both of the frequency of oscillation (or a shift thereof) and the damping voltage (or a shift thereof) can provide an indicator of the cloud point.

The cloud point of a petroleum-based composition 100 is defined herein as a particular point, usually defined in terms of a cloud-point temperature, at which some of the constituents of the petroleum-based composition such as paraffins or petroleum waxes first begin to precipitate, solidify or crystallize as the petroleum-based composition is cooled at a predetermined rate, generally in a range of about 0.2°–2° C./minute. If cooling is continued, the petroleum-based composition eventually possesses a viscosity at which it will not flow. The temperature at which this occurs under certain conditions is termed a freeze-point temperature or a solid-point temperature, with a pour-point temperature further being defined as a temperature about 3° C. above the freeze-point temperature. The cloud point is characterized by a rapid change in optical characteristics of the petroleum-based composition 100 which becomes cloudy or hazy at the cloud point due to constituents therein beginning to solidify or crystallize. Thus, the cloud-point temperature for a particular type of petroleum-based composition 100 (can provide an indication of the amount of paraffin or petroleum wax therein, which in turn an affect a quality (e.g. determined at least in part by a useful temperature range for use of the composition) and a market value of the petroleum-based composition.

Although the cloud point generally refers to the point at which constituents of the petroleum-based composition first begin to solidify, it will be understood that many types of petroleum-based compositions such as crude oil have a complex chemical structure, comprising a plurality of different chemical compounds or constituents, with each constituent having different characteristics including a different temperature at which it begins to solidify or crystallize. Thus, a sensitive enough instrument such as the acoustic-wave sensor apparatus 10 of the present invention can allow the determination of multiple points at which different constituents of a particular petroleum-based composition begin to solidify, thereby providing additional information about the petroleum-based composition.

Returning to FIG. 1, the electrical circuit 14 in some embodiments of the present invention can be an instrument such as a network analyzer, a frequency-sweep oscillator or the like for measuring frequency-response characteristic of the acoustic-wave device 12 near a resonant frequency thereof so that one or more electrical characteristics (e.g. capacitance, reactance, and resistance) of the device 12 can be determined by fitting the frequency-response characteristic to an equivalent-circuit model of the acoustic-wave device 12. The use of a network analyzer and a frequency-sweep oscillator for characterizing an acoustic-wave device is disclosed in the Granstaff et al patent (U.S. Pat. No. 5,201,215) which is incorporated herein by reference. By fitting the measured electrical characteristics of the TSM acoustic-wave device 12 to an equivalent circuit model, the accumulation of solidified constituents on one or both surfaces of the TSM acoustic-wave device 12 and a density-viscosity product of the petroleum-based composition in contact with the TSM acoustic-wave device 12 can be determined.

In the example of FIG. 1, the electrical circuit 14 provides an output signal 16 in response to the accumulation of solidified constituents on one or both surfaces of the TSM acoustic-wave device 12. The output signal 16 indicates one or more parameters of the acoustic-wave device 12 that depending on the particular type of acoustic-wave device 12 used for practice of the present invention can be a frequency of oscillation, a feedback or damping voltage, or a combination thereof. A calibration of the acoustic-wave device 12 can be performed by contacting one or more surfaces of the acoustic-wave device 12 with the petroleum-based composition 100 and measuring an unperturbed value of one or more parameters of the acoustic-wave device 12 in the absence of any solidified constituents. Alternately, the acoustic-wave device 12 can be calibrated prior to any contact with the petroleum-based composition 100. With a subsequent cooling of the petroleum-based composition 100 to produce solidified constituents therein, each parameter of the acoustic-wave advice 12 can then be measured as a deviation or shift from its unperturbed value (e.g. a shift in the frequency of oscillation; or a shift in the damping voltage; or both).

The output signal 16 is processed with a signal analyzer 20 (e.g. a frequency counter, a voltmeter, an analog-to digital converter, or the like) which can be connected to a signal processing unit 24 such as a computer or the like for analysis, data recordation, data display, or for providing an output for closed-loop feedback control for processing the petroleum-based composition 100. The signal processing unit 24 can further receive an input from a temperature readout 22 connected to the temperature sensor 18 to provide information about the temperature of the the petroleum-based composition for correlation with information generated by the acoustic-wave device 12 to determine a cloud point, pour point, or freeze point of the petroleum-based composition 100.

In the case of a TSM acoustic-wave device 12 as shown in the example of FIG. 1, a measurement of the frequency of oscillation (or a shift thereof) alone in some instances does not provide unique information about a thickness of an accumulation of solidified constituents on the surface(s) of the TSM acoustic-wave device 12. This is due to a compliant film (e.g. the solidified constituents comprising paraffin being accumulated on a surface of the TSM acoustic-wave device 12) behaving differently from a rigid film (e.g. the metal electrodes 28) deposited thereon. The rigid film deposited on a surface of the TSM acoustic-wave device 12 moves synchronously with the surface as the surface oscillates in a shear mode of vibration characterized by an in-plane displacement (i.e. motion parallel to the surface of the piezoelectric material). This motion of the rigid film produces a change in a stored or kinetic energy of the device 12 which decreases a resonant frequency of oscillation of the device 12 in proportion to an areal mass density (i.e. density times thickness) of the deposited rigid film. Since moving the rigid film does not result in a dissipation of energy, however, there is no measurable change in the damping voltage.

On the other hand, a compliant film (e.g. paraffin) is generally viscoelastic (i.e. having both an elastic character and a viscous character) with a lower portion of the compliant film moving synchronously with the surface on which it accumulates, and an upper portion of the compliant film that lags behind the motion of the surface. This lagging motion can produce a shear strain within the compliant film which can affect both an energy storage within the compliant film and an energy dissipation thereof. As the compliant film becomes thicker (e.g. due to an increased accumulation of the solidified constituents) the frequency of oscillation (or the shift thereof) which initially decreases due to an accumulation thereon can subsequently increase as the accumulation is further increased (see the curves in FIG. 4b). Thus, for some embodiments of the present invention, a combination of the frequency of oscillation (or the shift thereof) and the damping voltage (or the shift thereof) can be used for greater precision. The damping voltage is sensitive to both a change in the viscosity of the petroleum-based composition (e.g. due to precipitation of paraffins) and also to the accumulation of the paraffins on the surface of the TSM acoustic-wave device 12.

In some embodiments of the present invention, a second acoustic-wave device (not shown in FIG. 1) can be provided to compensate, at least in part, for a temperature dependence of the parameters of the acoustic-wave device 12. The second acoustic-wave device is preferably substantially identical to the acoustic-wave device 12 (i.e. a first acoustic-wave device) except for having surfaces isolated from contact with the petroleum-based composition 100. This can be achieved, for example, by forming the second acoustic-wave device on a common wafer or plate 26 with the first acoustic-wave device 12, with the second acoustic-wave device being overcoated with an isolation film of predetermined characteristics to prevent contact with the petroleum-based composition 100. Alternately, the second acoustic-wave device can be located proximate to the first acoustic-wave device 12 in a sealed enclosure that allows effective thermal contact with the petroleum-based composition 100, but not a physical contact. The sealed enclosure may further include a fluid of predetermined characteristics for matching a response of the second acoustic-wave device to that of the first acoustic-wave device 12 in the absence of any solidified constituents and/or for improving thermal contact with the petroleum-based composition 100. The second acoustic-wave device in these embodiments of the present invention operates in combination with the first acoustic-wave device 12 to provide the output signal 16 which can further comprise a difference in parameters of the first aid second acoustic-wave devices, including a difference in frequencies of oscillation, a difference in damping voltages, or a combination thereof.

Figure 2:
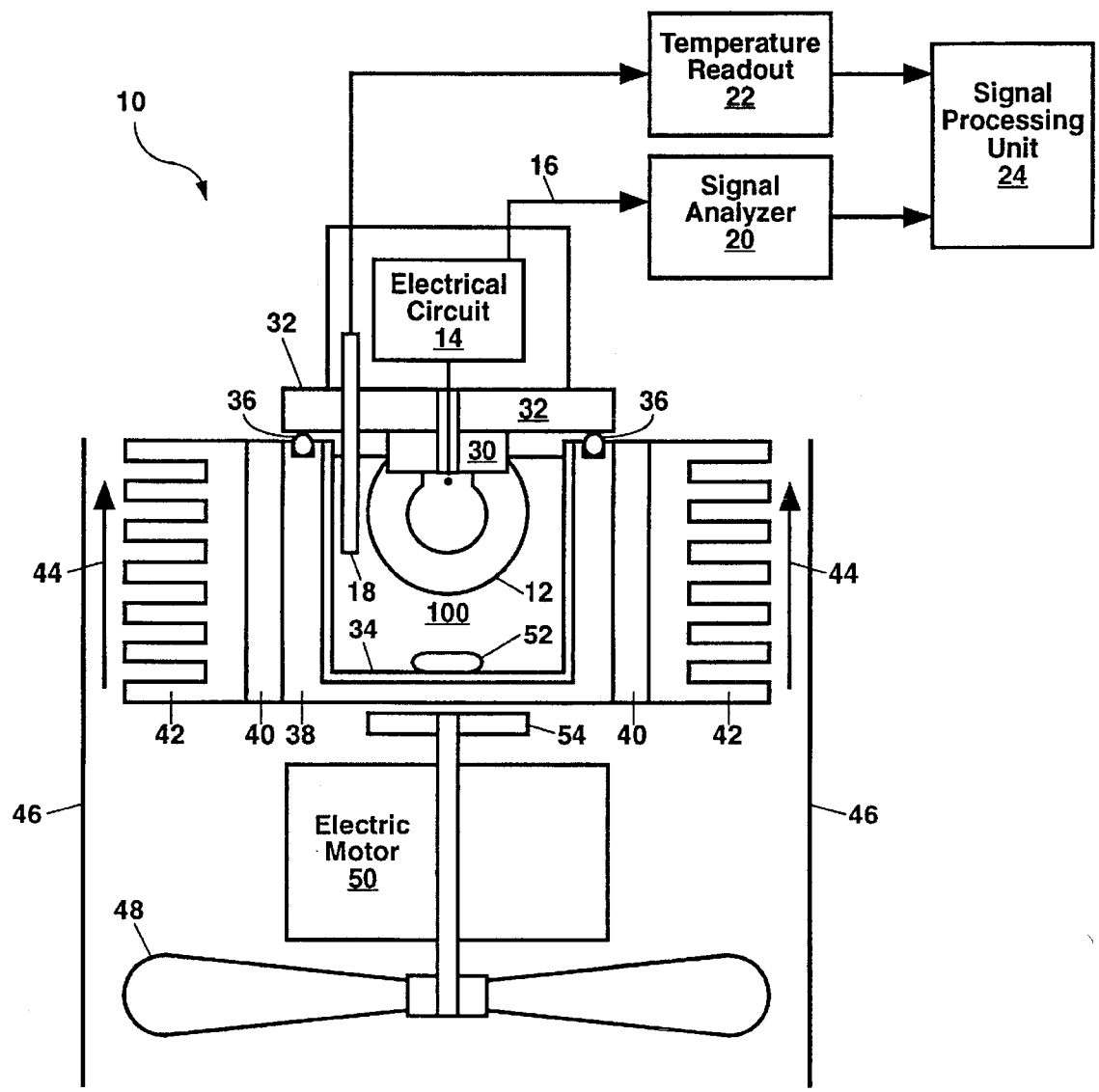
FIG. 2 shows a second embodiment of the present invention for analyzing a sample of a petroleum-based composition placed within a container.

FIG. 2 shows a second embodiment of the present invention for analyzing a sample of a petroleum-based composition 100 placed within a container. In FIG. 2, the apparatus 10 further comprises a container 34 (e.g. a glass, paper, plastic, fluorocarbon, or metal cup having a capacity of up to about 25 cm$^{-3}$ or more) for holding a sample of the petroleum-based composition 100 placed therein. Sealing means such as an O-ring 36 or the like can also be provided for sealing the container 34 to prevent escape of volatile constituents from the petroleum-based composition 100 at elevated temperatures. A pressure-relief valve can also be provided to prevent an over pressurization of the sample of the petroleum-based composition 100 at the elevated temperatures. And temperature-variation means are preferably provided for varying the temperature of the sample over a predetermined temperature range (e.g. about 0°–95° C.) which includes the cloud-point temperature.

The temperature variation means can comprise, for example, a thermally-conductive body 38 formed of a metal (e.g. stainless steel) or other thermally-conductive material for holding the container 34 and transferring heat to and/or from the sample of the petroleum-based composition 100 within the container 34. The body 38 can be shaped to provide a groove for supporting e O-ring 36 as shown in FIG. 2 and can further include fasteners or the like for securing the attachment plate 32 to the body 38 to seal the container 34.

Any means known to the art can be used for varying the temperature of the sample of the petroleum-based composition, including cooling the sample with a coolant (e.g. liquid or gaseous nitrogen, ammonia or a fluorinated hydrocarbon), or heating the sample with an electric heater. However, for portability of the apparatus 10, the temperature variation means can include one or more Peltier elements 40 (i.e. thermoelectric elements) in contact with the body 38 and electrically activated to control and vary the temperature of the sample of the petroleum-based composition 100. For a cube-shaped body 38 as shown in the second embodiment of the present invention in FIG. 2, Peltier elements 40 can be attached to each of four sides of the body 38 for effective heating and cooling thereof depending upon a direction of flow of an electrical current provided to the Peltier elements 40. The Peltier elements 40 can be controlled by a temperature controller (not shown) providing the electrical current in response to a feedback signal provided by the temperature readout 22; or a separate temperature sensor attached to the body 38 or placed within the container 34. The temperature controller allows the temperature of the petroleum-based composition sample to be maintained at a particular temperature at or above the cloud point, pour point or freeze point. Alternately, the temperature controller can be used in combination with the Peltier elements 40 for varying the temperature of the petroleum-based composition 100 (either upward or downward or both) over a predetermined temperature range that includes the cloud-point temperature. The temperature-variation step can be initiated, for example, in response to a signal provided by the signal processing unit 24 to the temperature controller, or by the temperature controller itself upon manual triggering.

For a cloud point determination, the sample is generally heated initially to a temperature at which any solidified constituents are dissolved (e.g. about 15° C. or more above an estimated cloud-point temperature for the petroleum-based composition 100); and then the sample is cooled at a predetermine rate generally about 0.2°–2° C./minute while measuring the output signal 16 from the acoustic-wave device 12 and the temperature as measured by the temperature sensor 18. For safety reasons, a temperature range for operation of the apparatus 10 is preferably limited to about 95° C. as a maximum temperature for the petroleum-based composition sample, and a minimum temperature is about 0° C. or less, limited only by the cooling capacity of the Peltier coolers 40.

In FIG. 2, waste heat generated by the Peltier elements 40 can be removed, for example, by heat sinks 42 attached to an outer surface of the elements 40 with the aid of an air flow 44 through a flue 46 provided by a fan blade 48. An electric motor 50 driving the fan blade 48 can also be used for agitating the sample of the petroleum-based composition 100 to maintain a uniformity of the sample below the cloud point temperature and to prevent any settling of the solidified constituents. The sample agitation can be provided, for example, by placing a stirring bar 52 within the container 34 and magnetically coupling the stirring bar 52 to a rotating magnet 54 attached to one end of the motor shaft.

Figure 3A:
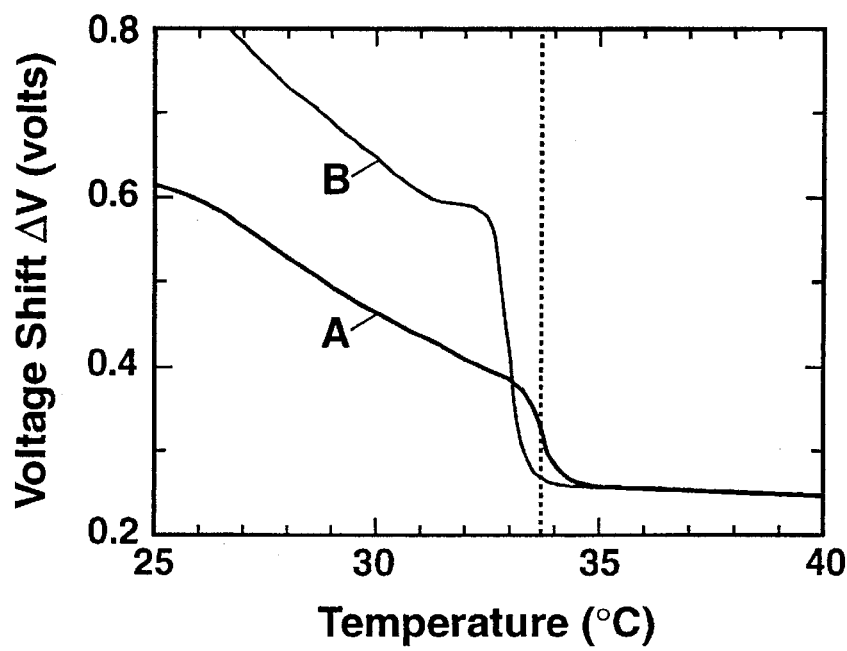
FIGS. 3a and 3b show measurements of a shift, ΔV, in a damping voltage and a shift, Δf, in a frequency of oscillation generated by the apparatus of the present invention as functions of the temperature of a paraffin/kerosine petroleum-based composition during cooling of the paraffin/kerosine composition at rates of 0.76° C./minute (thick-line curve) and 2.06° C./minute (thin-line curve), with dotted vertical lines to indicate a visually-measured cloud-point temperature for the paraffin/kerosine composition.
Figure 3B:
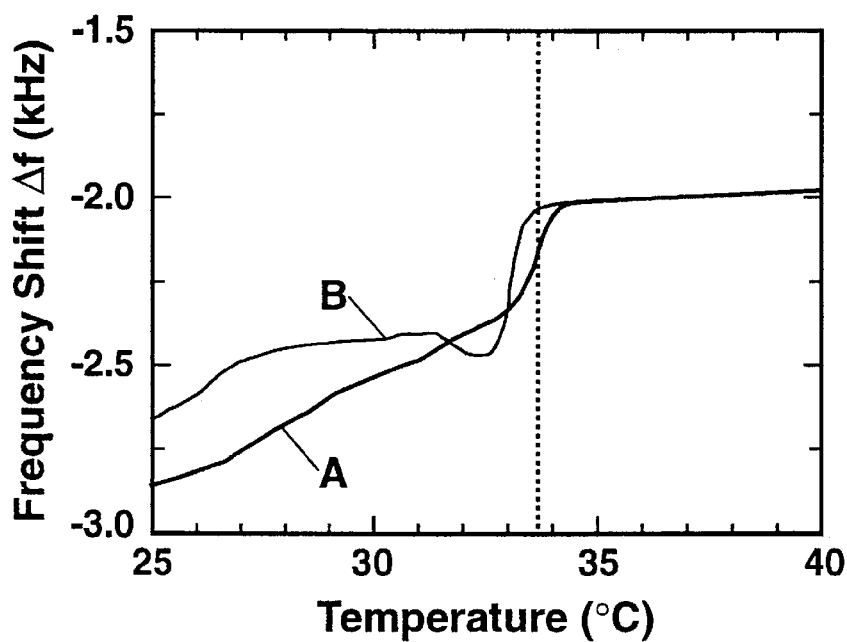

FIGS. 3a and 3b show measurements of a shift, $\Delta V$, in the damping voltage and a shift, $\Delta f$, in the frequency of oscillation, respectively, produced by the apparatus 10 of the present invention as functions of temperature for a sample of the petroleum-based composition 100 comprising paraffin dissolved in kerosine. To obtain the data shown in FIGS. 3a and 3b, a clean and dry TSM acoustic-wave device 12 was installed on the body 38 of the apparatus 10 of FIG. 2, and the output signal 16 was analyzed to provide information about an unperturbed frequency of oscillation of the device 12 and an unperturbed damping voltage provided to the TSM acoustic-wave device 12 by the lever oscillator electrical circuit 14.

The paraffin/kerosine sample was then placed in the container 34; and the container 34 was inserted into the body 38. The attachment plate 32 was fastened to the body 38 to contact the paraffin/kerosine sample 100 with the TSM acoustic-wave device 12, and to seal the sample to prevent escape of an y volatile constituents therein as the temperature was elevated to about 85° C. by the Peltier elements 40 and stabilized thereat. The temperature controller was then set to provide a predetermined cooling rate and data acquisition by the signal processing unit 24 was inserted to record data over time as the sample was cooled to below the cloud-point temperature, with the data comprising measurements of the shift, ΔV, in the damping voltage from its unperturbed or calibration value and the shift, Δf, in the frequency of oscillation from its unperturbed or calibration value.

Two data curves are shown in each of FIGS. 3a and 3b, with a thick-line curve labelled "A" representing measurements for cooling at a rate of 0.76° C./minute, and a thin-line curve labelled "B" representing measurements for cooling at a rate of 2.06° C./minute. Dotted vertical lines in FIGS. 3a and 3b represent a visually-measured cloud-point temperature for the paraffin/kerosine sample 100 for cooling at an intermediate rate of 1° C./minute.

In FIG. 3a, the damping voltage shift curves show an abrupt upturn or increase in slope near the visually-observed cloud-point temperature due to an onset of precipitation of paraffin (i.e. formation of the solidified constituents) from the petroleum-based composition 100. The precipitated paraffin both increases the viscosity of the petroleum-based composition 100 and accumulates on the surfaces of the TSM acoustic-wave device 12. After the paraffin accumulated on the surfaces of the TSM acoustic-wave device 12 exceeds a certain thickness as the temperature is further lowered, the damping voltage begins to saturate and the damping voltage curves in FIG. 3a show a downturn or decrease in slope. In FIG. 3b, the shift, Δf, in the frequency of oscillation is also affected, with the frequency shift becoming more negative near the visually-determine cloud-point temperature.

From the measurements in FIGS. 3a and 3b, an indication of the cloud-point temperature can be provided by the apparatus 10 at a point at which the curves first change slope as the sample of the petroleum-based composition 100 is cooled. According to this procedure for determining the cloud-point temperature with the apparatus 10, the cloud-point temperature is measured to be slightly higher for the lower cooling rate in FIGS. 3a and 3b. This is due to the lower cooling rate providing more time for nucleation of paraffin crystals to occur. Furthermore, for temperatures below the cloud-point temperature, the curves "A" and "B" show different behavior which is dependent on the particular cooling rates selected. This difference in behavior is thought to be due to dependence of properties of the solidified paraffin on the cooling rate, with a lower cooling rate leading to formation of paraffin crystals that are larger and more irregularly shaped and more aggregated than the paraffin crystals that are produced at a higher cooling rate.

Figure 4A:
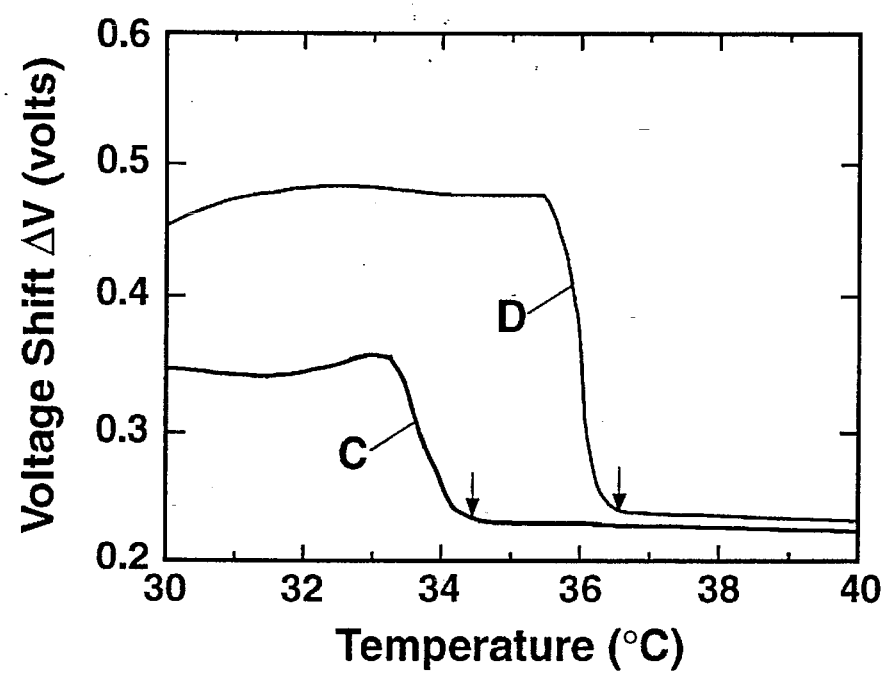
FIGS. 4a and 4b show measurements of the shift, ΔV, in the damping voltage and the shift, Δf, in the frequency of oscillation generated by the apparatus of the present invention as functions of temperature for two different paraffin/kerosine compositions cooled at the same rate (a first composition is indicated by the thick-line curve, and a second composition with added paraffin is indicated by the thin-line curve).
Figure 4B:
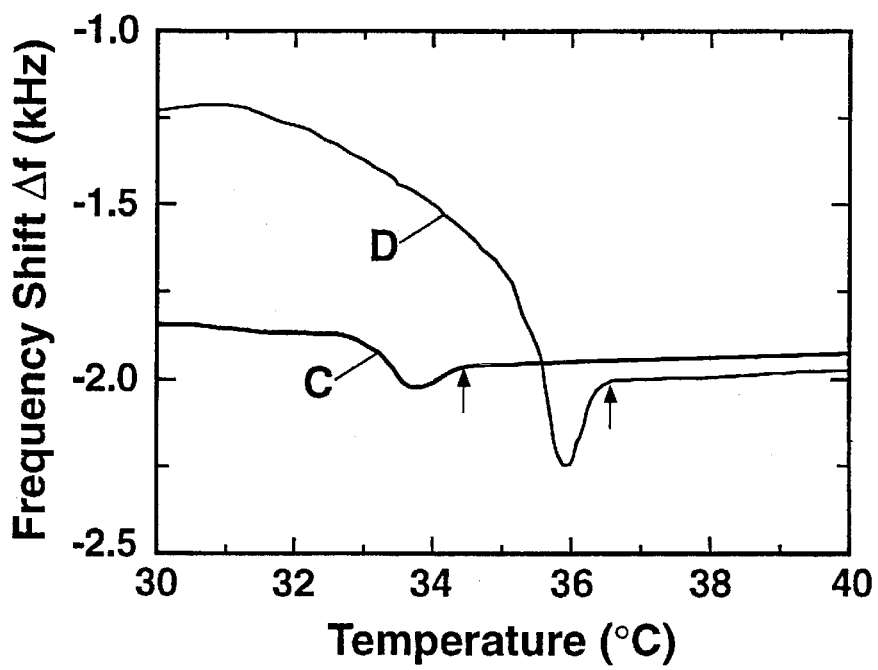

FIGS. 4a and 4b show measurements of the shift, ΔV, in the damping voltage and the shift, Δf, in the frequency of oscillation with the acoustic-wave sensor apparatus 10 of the present invention as functions of temperature for two different paraffin/kerosine compositions 100 cooled at the same rate (1° C./minute). In FIGS. 4a and 4b, the curves labelled "C" are for an initial sample of the petroleum-based composition 100 having a measured cloud-point temperature of 34.4° C.; while the curves labelled "D" are for the same sample having additional paraffin added thereto to raise the measured cloud-point temperature to 36.6° C. (The measured cloud-point temperatures for each curve as determined by the acoustic-wave sensor apparatus 10 is indicated by a vertical arrow.)

The measurements in FIGS. 4a and 4b show that the the cloud-point temperature for a particular petroleum-based composition depends on the amount of dissolved solids (e.g. paraffin) therein that can solidify as the petroleum-based composition is cooled. Since paraffins or petroleum waxes have a limited solubility in each particular petroleum-based composition, they will generally precipitate out or solidify at a temperature (i.e. the cloud-point temperature) that is determined by the amount and chemical composition of the paraffins. Furthermore, the cloud-point temperature is somewhat dependent on a thermal history for the petroleum-based composition, with slightly different cloud-point temperatures generally being measured depending on whether the petroleum-based composition is cooled down from a temperature above the cloud point or heated up from a temperature below the cloud point. Finally, for some petroleum-based compositions, a change in properties at the cloud point can be small and can occur over a limited range of temperature. For these petroleum-based compositions, it may be preferable to use the acoustic-wave sensor apparatus 10 to provide more than one indication of the cloud-point temperature (i.e. a range of cloud-point temperatures over which different constituents begin to precipitate or solidify). Furthermore, these acoustic-wave sensor measurements can be correlated with other measurements made at the same time, for example, from an analysis of a temperature-versus-time curve using the temperature sensor 18. These other measurements can also include observing a deviation in a cooling rate curve from linearity when the apparatus 10 is set to cool the petroleum-based composition sample at a predetermined fixed rate (i.e. cooling a fixed number of °C./minute) since the temperature at which a deviation in the cooling rate curve first appears also correlates with the cloud-point temperature. Alternately, the temperature controller can be set to provide a constant cooling rate and the power applied to the Peltier elements 40 can be recorded and analyzed (e.g. by the signal processing unit 24) for a deviation which occurs at the cloud-point temperature. At the cloud point more power must be applied to the Peltier elements 40 to maintain the constant cooling rate since additional heat is generated at the cloud point within the petroleum-based composition 100 by solidification of the paraffin (i.e. a heat of fusion).

In FIG. 4a, the shift, ΔV, in the damping voltage provides a good indication of the cloud-point temperature for each paraffin/kerosine composition 100. In FIG. 4b, the frequency shift curves are more complicated due to the frequency of oscillation initially decreasing as the paraffin is accumulated on the TSM acoustic-wave device 12, and then increasing after reaching a certain accumulated layer thickness. However, in both FIGS. 4a and 4b, large changes are observed in each of the parameters as the sample is cooled to the cloud-point temperature. Thus, the acoustic-wave sensor apparatus 10 of the present invention provides a means for cloud point determination that is less subjective and less dependent on a particular operator than prior-art visual methods. Furthermore, the acoustic-wave sensor apparatus 10 has an advantage of being equally well suited to measurements of transparent and opaque samples of petroleum-based compositions.

A determination of characteristics of petroleum-based compositions including the cloud point, pour point and freeze point is important for evaluating or designing recovery, handling, transportation and refining systems for petroleum-based composition. Furthermore, these characteristics determine, at least in part, a temperature range for usage each petroleum-based composition and thus market value for each petroleum-based composition. During recovery, transport, storage and refining of crude oil any exposure to equipment, pipelines or wellbores at temperatures below the cloud-point temperature can lead to a solidification of constituents (e.g. paraffin or petroleum wax)

from the crude oil and a deposition of the solidified constituents on cooler surfaces of the equipment, pipelines or wellbores. The solidified constituents can limit system capacity and require provision for removal of the solidified constituents by heat, chemicals, or mechanical scraping. Furthermore, dehydration of a waxy crude below its cloud point is generally not efficient because some of the precipitated wax concentrates at an oil/water interfaced and builds a rag layer that does not allow movement of water, thereby reducing an efficiency for dehydration which can only be corrected by an increased temperature.

Figure 5:
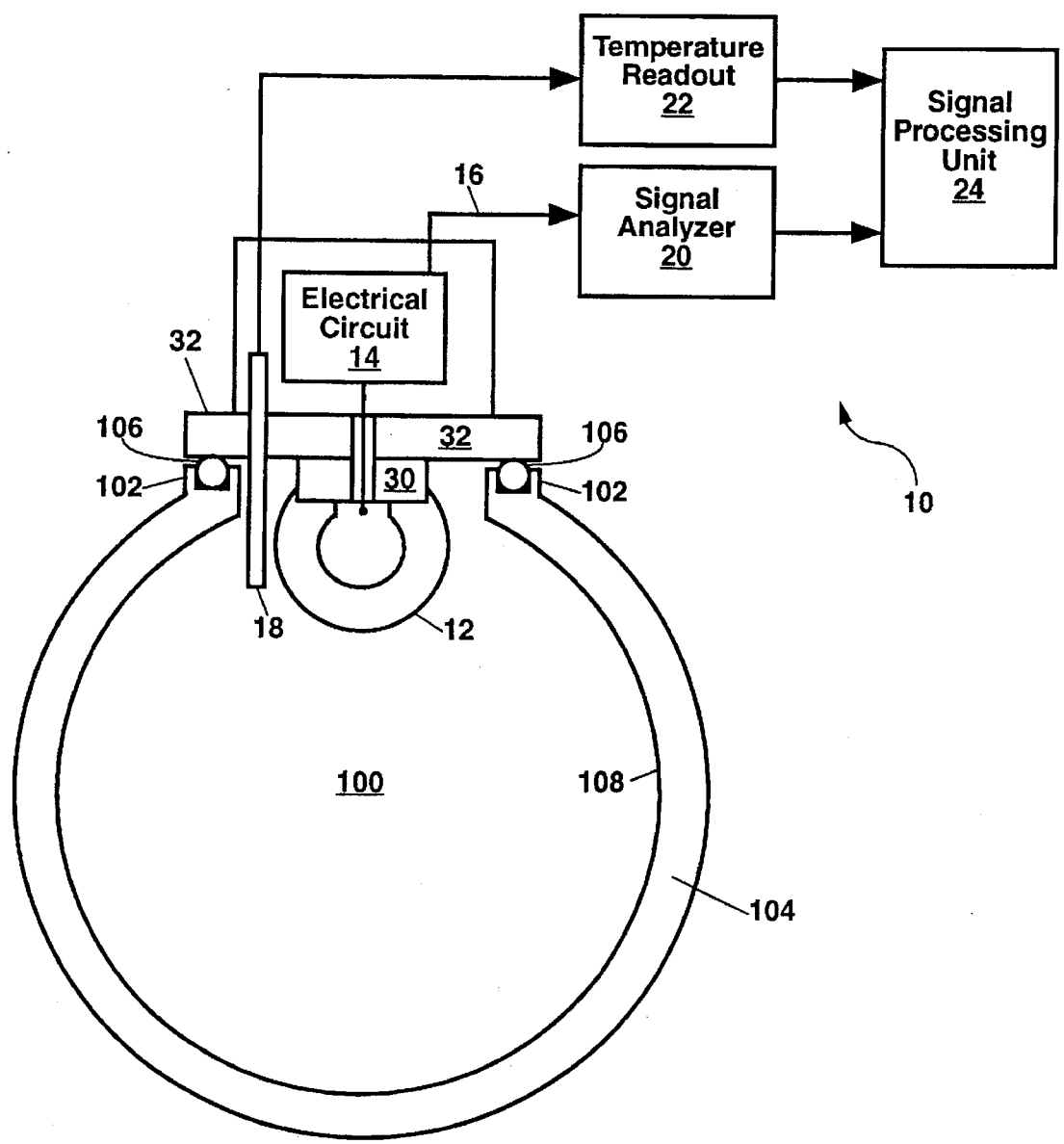
FIG. 5 shows a third embodiment of the present invention for analyzing a petroleum-based composition within a pipeline or storage tank.

FIG. 5 shows a third embodiment of the present invention suitable for analyzing a petroleum-based composition in a pipeline or storage tank. In FIG. 5, the acoustic-wave sensor apparatus 10 is shown attached, at least in part, to a flanged opening 102 in a pipeline 104 (shown in a cross-sectional view) with an O-ring 106 or the like and one or more fasteners (not shown) provided to seal the attachment plate 32 of the apparatus 10 to the flanged opening 102. A similar arrangement an be used for attaching the acoustic-wave sensor apparatus 10 to a tank.

The acoustic-wave sensor apparatus 10 according to the third embodiment of the present invention can be used for sensing changes in fluid properties within a pipeline or storage tank that occur at the cloud point (e.g. formation of a slurry of solidified constituents which increases the viscosity of the petroleum-based composition 100) or to sense an accumulation of solidified constituents on an inner surface of the pipeline or storage tank. Furthermore, the apparatus 10 can be used for analyzing a characteristic of the petroleum-based composition 100 such as a cloud-point temperature a pour-point temperature or a freeze-point temperature.

By monitoring the output signal 16 from the acoustic-wave device 12 as a function of time to measure an accumulation of solidified constituents from the petroleum-based composition 100 on one or more surfaces of the acoustic-wave device 12, the apparatus 10 can provide an indication of solidification of the constituents on an inner surface 108 of the pipeline 104 (or alternately an inner surface of a storage tank). Such solidification can occur when the temperature of the petroleum-based composition is reduced below the cloud-point temperature, or when the cloud-point temperature is raised above the temperature of the petroleum-based composition due to an excess of paraffin or wax in the composition 100 (e.g. during crude oil recovery). This type of monitoring can be performed without the temperature sensor 18, although the provision of a temperature sensor 18 is generally to be preferred since it provides additional information about the temperature, of the petroleum-based composition 100 (e.g. for quantifying the cloud-point temperature, or for determining whether the cloud point was attained due to a drop in temperature or due to an increase in paraffin content of the petroleum-based composition).

For the third embodiment of the present invention in FIG. 5, means such as a heater (not shown) or the like may be provided proximate to the acoustic-wave device 12 for periodically removing e accumulation of solidified constituents from the acoustic-wave device 12. Such a heater could be provided, for example, as a thin-film or thick-film resistance element on a common wafer or plate 26 with the acoustic-wave device 12; or as a heating element in thermal contact with the support 30 or a portion of the petroleum-based composition 100 in contact with the acoustic-wave device 12.

The third embodiment of the present invention in FIG. 5 can also be operatively connected to means for maintaining the petroleum-based composition 100 above or below a predetermined point such as the cloud point, the pour point or the freeze point; or above or below a predetermined product of density times viscosity. As an example, the acoustic-wave sensor apparatus 10 could be located on a sea-floor well head to detect when crude oil being recovered is below a cloud point, with the information provided by the apparatus 10 being used to signal an alarm, or to initiate or increase a chemical injection or heat injection into the wellbore to raise the crude oil above the cloud point. Such chemical injection could be in the form of any additive known to the art, including a solvent for dissolving at least in part the solidified constituents; surfactant or dispersant for limiting or preventing aggregation of the solidified particles; or a crystal modifier that acts as a cloud seed to provide more sites for precipitation of the solidified constituents so that large crystals do not form. This would improve crude oil recovery by reducing production costs and also the cost of controlling paraffin deposition.

Similar improvements are expected for refining petroleum-based constituents (or during use thereof). For example, the apparatus and method of the present invention could be used within a refinery, with the acoustic-wave sensor apparatus 10 signaling an alarm when a petroleum-based constituent within a pipeline or storage tank reaches the cloud point. Alternately, the apparatus 10 could be used in a closed-loop feedback mode (e.g. with an output from the signal processing unit 24) to maintain a petroleum-based composition above a predetermined point (e.g. the cloud point) by chemical injection, or by heat injection, or by filtering (including centrifuging) the petroleum-based composition to remove at least a portion of any solidified constituents therein, or by blending the petroleum-based composition with an additive as described heretofore or with another batch of a hydrocarbon composition having a smaller quantity of constituents that solidify (e.g. blending different batches of petroleum-based compositions to provide a predetermined cloud-point temperature for a product). In this way, the apparatus 10 of the present invention can provide precise measurements to allow a closer regulation of refining or processing to maximize yield and reduce a cost for refining without sacrificing quality.

The matter set forth in the foregoing description and accompanying drawings is offered by way of illustration only and not as a limitation. Other applications and variations of the acoustic-wave sensor apparatus and method will become evident to those skilled in the art. For example, although the acoustic-wave device 12 is shown extending outward from the support 30 in FIGS. 1 and 5, in other embodiments of the present invention, the acoustic-wave device can be mounted with surfaces parallel to a flow direction, or flush-mounted with only a single exposed surface thereof. Furthermore, in some embodiments of the present invention, the temperature sensor 18 (e.g. a platinum resistance temperature sensor, i.e. RTD) may be formed alongside the acoustic-wave device on the piezoelectric plate or wafer. Thus, the actual scope of the invention is intended to be defined in the following claims when viewed in their proper perspective based on the prior art.

The invention claimed is:

1. An apparatus for analyzing a normally liquid petroleum-based composition having constituents which solidify upon being cooled below a cloud-point temperature, the apparatus comprising: a first acoustic-wave sensing means having at least one surface in contact with the petroleum-based composition for detecting the presence of the solidified constituents in a soft or semi-rigid state accumulated thereon and non-rigidly adhered thereto and for generating an output signal in response to the accumulation.

2. The apparatus of claim 1 further including a temperature sensing means in contact with the petroleum-based composition for measuring the temperature thereof.

3. The apparatus of claim 1 further including a support for holding the acoustic-wave sensing means and making electrical contacts thereto.

4. The apparatus of claim 1 further comprising electrical circuit means connected to the first acoustic-wave sensing means for activating the acoustic-wave sensing means and for generating the output signal therefrom.

5. The apparatus of claim 4 wherein the output signal indicates a parameter of the first acoustic-wave sensing means selected from the group consisting of a frequency of oscillation, a shift in the frequency of oscillation, a damping voltage, a shift in the damping voltage, and a combination thereof.

6. The apparatus of claim 4 further including a second acoustic-wave sensing means substantially identical to the first acoustic-wave sensing means except for having surfaces isolated from contact with the petroleum-based composition, the first and second acoustic-wave sensing means operating in combination to provide the output signal.

7. The apparatus of claim 6 wherein the output signal comprises a difference in parameters of the first and second acoustic-wave sensing means selected from the group consisting of a difference in frequencies of oscillation, a difference in damping voltages, and combinations thereof.

8. The apparatus of claim 4 wherein the electrical circuit means is located at least in part proximate to the first acoustic-wave sensing means within a housing.

9. The apparatus of claim 4 wherein the first acoustic-wave sensing means is selected from the group consisting of thickness-shear-mode devices, surface-acoustic-wave devices, acoustic-plate-mode devices, and flexural-plate-wave devices.

10. The apparatus of claim 1 wherein the solidified constituents comprise paraffin.

11. The apparatus of claim 1 wherein the solidified constituents comprise alkane components of petroleum having a chain length of about $C_{20}$ or greater.

12. The apparatus of claim 1 wherein the apparatus provides analysis information about the petroleum-based composition selected from the group consisting of a cloud-point determination, a pour-point determination, a freeze-point determination, and combinations thereof.

13. The apparatus of claim 1 further including means for varying the temperature of the petroleum-based composition over a predetermined temperature range including the cloud-point temperature.

14. The apparatus of claim 13 further including mixing or homogenizing means for agitating the petroleum-based composition.

15. The apparatus of claim 1 further including means for periodically removing the accumulated solidified constituents from the acoustic-wave sensing means.

16. The apparatus of claim 1 wherein the petroleum-based composition has a viscosity of at least 10 centipoises (cP) at the cloud-point temperature.

17. The apparatus of claim 1 wherein the output signal is operatively connected to means for maintaining the petroleum-based composition above a predetermined point selected from the group consisting of a cloud point, a pour point, and a freeze point.

18. The apparatus of claim 1 wherein the output signal is operatively connected to means for maintaining the petroleum-based composition above a predetermined multiplicative product of density times viscosity.

19. An apparatus for sensing solidification of constituents within a normally liquid hydrocarbon composition comprising:
 a) an acoustic-wave device in contact with the hydrocarbon composition; and
 b) an electrical circuit for activating the acoustic-wave device to produce an output signal therefrom that varies in response to solidification and non-rigid adherence of the constituents in a soft or semi-rigid state.

20. The apparatus of claim 19 further including a temperature sensor in contact with the hydrocarbon composition for measuring the temperature thereof.

21. The apparatus of claim 19 wherein the acoustic-wave device is selected from the group consisting of thickness-shear-mode devices, surface-acoustic-wave devices, acoustic-plate-mode devices, and flexural-plate-wave devices.

22. The apparatus of claim 19 wherein the output signal provides analysis information about the hydrocarbon composition selected from the group consisting of a cloud-point determination, a pour-point determination, a freeze-point determination, and combinations thereof.

23. The apparatus of claim 19 further including means for varying the temperature of the sample over a predetermine temperature range including a cloud-point temperature.

24. The apparatus of claim 19 wherein the output signal is operatively connected to means for maintaining the hydrocarbon composition above a predetermined point selected from the group consisting of a cloud point, a pour point, and a freeze point.

25. A method for analyzing a normally liquid petroleum-based composition having constituents which solidify upon being cooled below a cloud-point temperature comprising steps for:
 a) contacting the petroleum-based composition with at least one surface of an acoustic-wave device; and
 b) activating the acoustic-wave device with an electrical circuit and measuring at least one parameter thereof according to an output signal of the acoustic-wave device which varies in response to solidification and non-rigid adherence of the constituents in a soft or semi-rigid state.

26. The method of claim 25 further including a step for varying the temperature of the petroleum-based composition over a predetermined temperature range including the cloud-point temperature.

27. The method of claim 26 further including steps for measuring and recording the temperature of the petroleum-based composition.

28. The method of claim 27 further including a step for constructing a temperature-versus-time curve showing the variation of the temperature of the petroleum-based composition with time and noting any deflections in a slope of the temperature-versus-time curve.

29. The method of claim 25 wherein the step for activating the acoustic-wave device comprises applying a radio-frequency (rf) electrical signal to the device and exciting an acoustic vibration mode therein.

30. The method of claim 29 wherein the radio-frequency (rf) electrical signal is applied to the acoustic-wave device by connecting the device to the electrical circuit and with an electrical circuit coupling designed such that the acoustic-wave device forms a feedback frequency-control element of the electrical circuit.

31. The method of claim 25 wherein the step for measuring the parameter of the acoustic-wave device includes measuring a change of the parameter from an unperturbed value thereof in the absence of the solidified constituents.

32. The method of claim 25 wherein the measured parameter of the acoustic-wave device is selected from the group consisting of a frequency of oscillation, a shift in the frequency of oscillation, a damping voltage, a shift in the damping voltage, or a combination thereof.

33. The method of claim 25 wherein the step for contacting the petroleum-based composition includes placing a sample of the petroleum-based composition in a container and varying the temperature of the sample over a predetermined temperature range.

34. The method of claim 33 wherein the predetermined temperature range includes the cloud-point temperature.

35. The method of claim 33 wherein the temperature is varied at a rate of about 0.2°–2° C. per minute.

36. The method of claim 33 further including a step for calibrating the acoustic-wave device in the absence of contact with the petroleum-based composition.

37. The method of claim 25 further including a step for maintaining the petroleum-based composition above a predetermined temperature.

38. The method of claim 37 wherein the predetermined temperature is selected from the group consisting of a cloud-point temperature, a pour-point temperature, and a freeze-point temperature.

39. The method of claim 38 wherein the step for maintaining the petroleum-based composition above the predetermined temperature comprises filtering the petroleum-based composition to remove at least a portion of any solidified constituents.

40. The method of claim 38 wherein the step for maintaining the petroleum-based composition above the predetermined temperature comprises adding an additive to the petroleum-based composition.

41. The method of claim 40 wherein the additive is selected from the group consisting of a solvent, a dispersant, a surfactant, a crystal modifier, or combinations thereof.

42. The method of claim 40 wherein the additive has a smaller quantity of constituents which solidify than the petroleum-based composition.

43. The method of claim 25 further including a step for maintaining the petroleum-based composition above a predetermined density-viscosity multiplicative product.

44. The method of claim 25 further including a step for removing any solidified constituents from the surface of the acoustic-wave device.

* * * * *